(12) United States Patent
Wendelken et al.

(10) Patent No.: US 6,193,658 B1
(45) Date of Patent: Feb. 27, 2001

(54) METHOD AND KIT FOR WOUND EVALUATION

(76) Inventors: Martin E Wendelken, P.O. Box 176, New Milford, NJ (US) 07646; Charles L. Pope, 199 Donald Rd., Guilford, CT (US) 06437

( * ) Notice: Subject to any disclaimer, the term of this patent is extended or adjusted under 35 U.S.C. 154(b) by 0 days.

(21) Appl. No.: 09/339,668

(22) Filed: Jun. 24, 1999

(51) Int. Cl.$^7$ .................................................. A61B 08/00
(52) U.S. Cl. ............................................................ 600/437
(58) Field of Search ........................... 600/437, 43, 449; 602/58, 52; 601/1

(56) References Cited

U.S. PATENT DOCUMENTS

| | | | |
|---|---|---|---|
| 4,535,782 | * | 8/1985 | Zoltan .................................. 128/655 |
| 5,152,757 | * | 10/1992 | Eriksson ............................... 604/305 |
| 5,265,605 | * | 11/1993 | Afflerbach ............................ 128/630 |
| 5,270,168 | * | 12/1993 | Grinnell ............................... 435/7.21 |
| 5,702,356 | * | 12/1997 | Hathman ................................. 602/41 |
| 5,749,842 | * | 5/1998 | Cheong, Rigby ....................... 602/41 |
| 5,910,125 | * | 6/1999 | Cummings et al. .................... 602/58 |
| 6,007,499 | * | 12/1999 | Martin et al. ............................ 601/3 |
| 6,066,773 | * | 5/2000 | Freeman ................................ 605/52 |

* cited by examiner

*Primary Examiner*—Marvin M. Lateef
*Assistant Examiner*—Maulin Patel

(57) ABSTRACT

A method and kit for the evaluation of wounds or ulcers (14) using ultrasound that allows an examiner to measure a wound (14) along with adjacent soft tissue structures (16) and bone (22) including tendon, ligaments, and muscle. This same method and kit contains gel (30) and an adhesive flexible film (32) which has a duo function and serves as a protective barrier preventing cross contamination between transducer (10) and ulcer (14), while allowing unimpeded conduction of ultrasound transmission to tissues (16) and subsequent echoes received from tissues (16) to be evaluated and recorded by a health care practitioner.

3 Claims, 3 Drawing Sheets

METHOD AND KIT FOR WOUND EVALUATION

1. FIELD OF INVENTION

The field of this invention relates to a method and a kit for the evaluation of wounds, in order to determine treatment efficacy, to uncover hidden pathologies, and to monitor and record the healing process.

2. BRIEF DESCRIPTION OF PRIOR ART AND BACKGROUND OF THE INVENTION

There are a number of different types of wounds. Some are superficial, occurring in the first few layers of skin, while puncture wounds involve an object pushed through the skin. Wounds known as ulcers are missing a number of layers of skin, usually are cavernous, and can be found on all areas of the body. The etiology of a particular ulcer can vary greatly, and therefore such wounds have different nomenclature which is related to the diagnosis. For example, decubitus ulcers (know as bedsores) are commonly found on the sacrum, while neurotrophic ulcers have a predilection for the feet of diabetics. As the cause of an ulcer is determined, a treatment regimen and wound care of various ulcers will differ accordingly.

In treating wounds, part of the care includes an objective assessment of each wound. This evaluation includes, but is not limited to, the color, odor, temperature, condition of tissue (i.e. macerated, dry, and presence of exudate) and condition of wound dressing. If a wound is an ulcer, its size, depth and volume are of importance. It is obvious that a recorded assessment gives a treating medical practitioner a history and progress report of wound healing, which in turn is a direct reflection of a chosen treatment regimen.

Within assessment parameters, a number of methods for diagnosing and treating wounds have evolved. Patents such as U.S. Pat. No. 5,270,168 (1993) Grinnell; measures proteases to diagnose non-healing ulcers and U.S. Pat. No. 5,152,757 (1992) Eriksson; describes a chamber and system for diagnosis and treatment of wounds. Other patents concentrate on measuring a wound itself as a key factor as to how effective a treatment plan is on curing that particular wound. In the past, various methods for measuring ulcers have been employed. One such method is the utilization of a simple ruler that is placed over a wound recording its length and width. A second measurement includes the act of placing this same identical ruler in the vertical plane, which is inserted into a wound resulting in a recorded depth measurement. U.S. Pat. No. 5,749,842 (1998) Cheong & Rigby; disclose and describe a packet containing a wound dressing and a method for measuring the area of a wound.

Another method of wound assessment is to determine the volume of an ulcer by filling a tissue defect with various substances such as molding material. After filling a wound and once hardened, the molding material is then removed from a wound site and measured. An ulcer's volume in this example is equal to the volume of the hardened mold. The disadvantages of this molding method are that it is painful to a patient and disregards good sterile technique.

A less painful and less accurate method to determine volume involves filling an ulcer with fluid such as normal saline and noting the volume of fluid used.

Still another less painful and less invasive method to measure ulcer volume utilizes stereophotogrammetric instrumentation. This method requires the exact angles of two cameras focused on a wound followed by viewing and measuring the negatives to attain a particular ulcer volume.

Another U.S. Pat. No. 4,535,782 (1985) Zoltan; optically projects a visual matrix at known angles and distances into a wound allowing the volume of an ulcer to be determined.

There are numerous other patents disclosed which are used to allow assessment of wounds. Some like U.S. Pat. No. 5,265,605 (1993) Afflerbach; provide a wound assessment sheet and graph for tracing wound margins, while U.S. Pat. No. 5,702,356 (1997) Hathman; provides for a wound dressing that can be opened and resealed for the purpose of assessment and application of medication.

Further companies such as 3M, and Smith & Nephew produce transparent dressings like Tegaderm™ and Opsite™ (respectively), that provide as part of their packaging material a grid to be used to measure a wound during assessment.

Although these methods are novel for their intended purposes, they fail to provide a practitioner with vital information about a number of conditions that may occur in and around a wound site. Other aforementioned methods such as producing a mold of a wound are painful when performed and are inaccurate in measurement. Furthermore, stereophotogrammetic techniques and optically projected matrix procedures require precise measurements and angles leading to errors in calculations. Using external grids to measure open wounds or providing graphs and assessment sheets fail to give a practitioner vital information about what is occurring below a wound surface. This is true whether a wound is an open ulcer or closed superficial and or puncture wound.

The present invention provides a method and kit for examining wounds using ultrasound. This novel method provides for measuring of volumes of open wounds along with their surface area. In addition using this same method and kit allows for measuring and assessing a wound site below its surface along with the area surrounding it, both of which cannot be see by human eye. For example, assessment and measurement of an ulcer's base thickness (or floor) can be determined. Adding this novel dimension in evaluating ulcers, many of which occur over a bony prominence, will reveal if a wound is close to the surface of a bone or has penetrated a bone. Additionally, this method and kit for examination of wounds allows a practitioner to find other hidden and potential pathology that may occur below the surface of a closed wound or beyond the wall of an ulcer that cannot be seen using present methods. Tissue destruction such as a subcutaneous abscess, or a sinus tract causing lateral channeling/tunneling of a wound margin can be observed and documented. Even further, this method and kit greatly reduce the of risk cross contamination of a wound and an ultrasound transducer. This method and kit allows subcutaneous evaluation of a wound and local tissues that cannot be seen by eye from the outside surface of a wound. Finally, this method and kit unlike other testing methods, that rely on the circulation of injected dyes or radioisotopes, allows an evaluation of a wound independent of arterial or venous blood flow.

3. OBJECTIVES AND ADVANTAGES

This unique disclosed method and kit, using ultrasound, has the ability to fulfill the needs of a health care practitioner. This method and kit provides a detailed examination of all wounds including their surrounding soft tissue and other local anatomical structures.

A principal objective of this method and kit is to provide for an exact measurement of a wound including size, volume, and surface area.

Another objective of this method and kit is to provide examination of a wound itself including its base and surrounding walls.

Still another objective of this method and kit is to provide an examiner with the ability to measure the thickness of the base of a wound especially when located over a bone or a mass.

Another objective of this method and kit is to allow a practitioner to perform a non-invasive examination of soft tissue adjacent to a wound for destructive processes that might be occurring below the skin surface and around a wound site which cannot be seen by human eye.

Still another objective of this method and kit is to provide this information without causing pain to a patient or harm to tissues.

A further objective is to use this method of examination and kit to determine if a present treatment regimen is effective promoting closure of a wound.

Yet another objective of this method and kit is to prevent cross contamination of a wound and the surface of an ultrasound transducer.

Another objective of this method and kit is to use an imaging technique that is safe, non-invasive, and requires no radiation, magnetic flux, or dyes.

Still another objective of this method and kit is to provide a vehicle to sequester or separate infected gel, which will minimize the risk of transmission of microorganisms.

Yet another objective of this method and kit is to allow a practitioner to scan a wound that lacks blood supply. Other procedures have to rely on blood flow to carry invasive dyes, radioisotopes, or other substances to a wound before it can be scanned.

BRIEF DESCRIPTION OF DRAWINGS

By using this method and kit, these objectives will become apparent with the following description and clarified with referral to the drawings provided.

Figure 1:
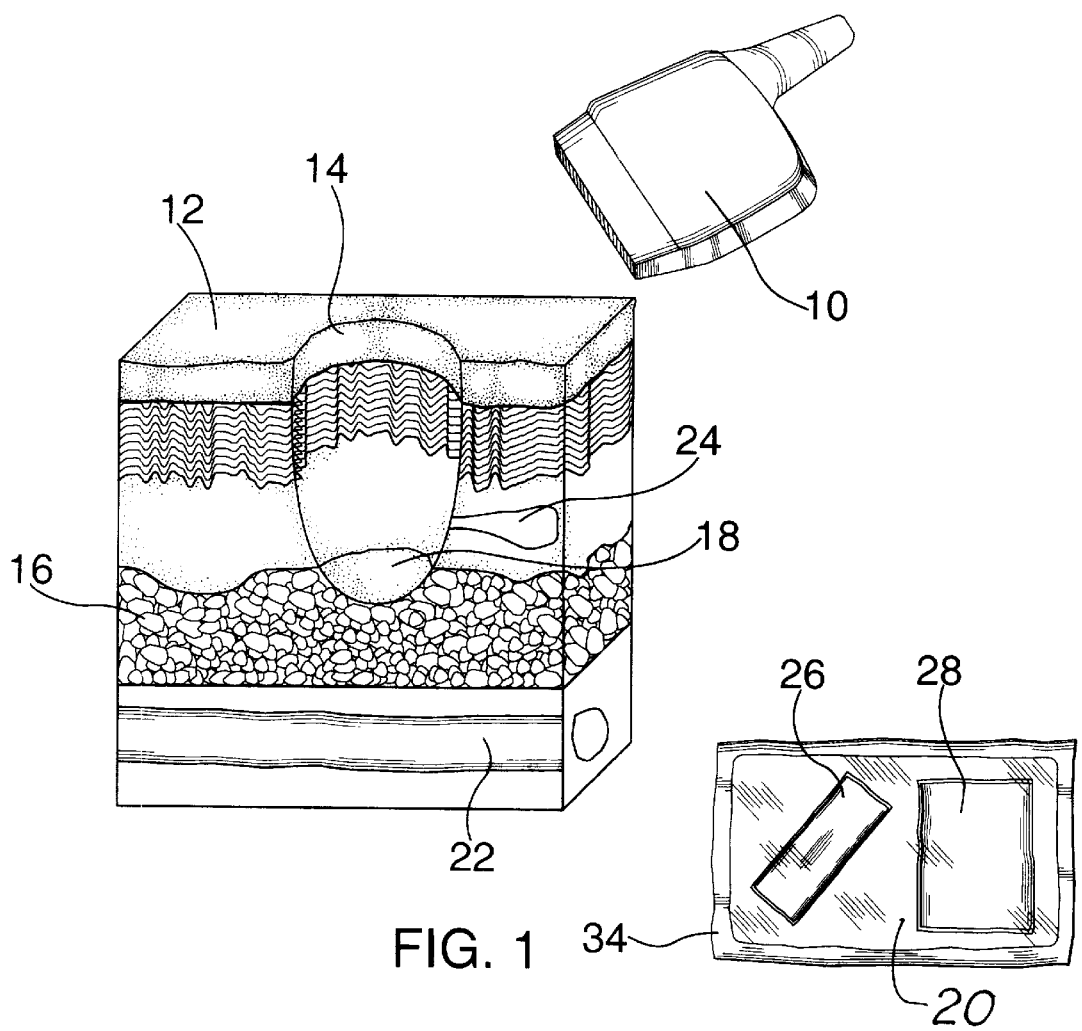
FIG. 1 is a cross sectional view of an ulcer with a bone below it. Also included in FIG. 1 is a picture of a typical transducer used in ultrasound, a kit containing a packet of sterile gel, and a packet with a sterile adhesive flexible film.

| Reference Numerals in Drawings | |
|---|---|
| 10 ultrasound transducer | 12 skin |
| 14 ulceration/wound | 16 subcutaneous tissue |
| 18 base ulcer | 20 envelope |
| 22 bone below ulcer | 24 subcutaneous abscess |
| 26 packet of sterile water soluble gel | 28 packet of adhesive flexible film |

| -continued | |
|---|---|
| Reference Numerals in Drawings | |
| 30 transmission gel | 32 adhesive flexible film |
| 34 kit containing packet of gel and packet of adhesive flexible film | |

DESCRIPTION OF EMBODIMENT—FIGS. 1 to 5

Referring to FIG. 1, using method and kit 34. Kit 34 is preferably supplied in sterile packaging and is comprised of an envelope 20 that contains two packets. The first packet contains sterile water-soluble gel 26 and a second packet that has sterile flexible adhesive film 28. Also in this figure observe a typical block of soft tissue that has a wound, ulceration 14. Ulcer 14, as it appears in FIG. 1, illustrates that a number of layers of skin 12 are missing and has penetrated deep into subcutaneous tissue 16 just above bone 22. Extending from sidewall of ulcer 14, FIG. 1 demonstrates a pathological condition, (an infection) or abscess 24. Observe that base of ulcer 18 extends into subcutaneous tissue 16 and one can conclude from FIG. 1 that base of ulcer 18 has not penetrated to the surface of bone 22. Finally, FIG. 1 introduces an ultrasound transducer 10, which is used to scan ulcer 14 and adjacent skin 12, subcutaneous tissue 16, and bone 22. Although transducer 10 appears to be a linear array transducer, any type of ultrasound transducer such as a phased array sector transducer could be utilized.

Figure 2:
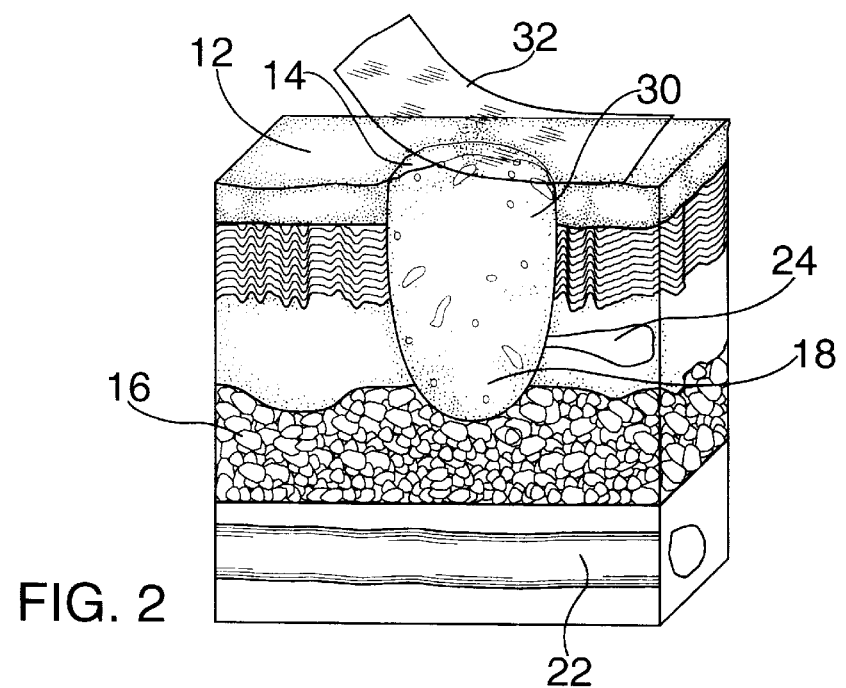
FIG. 2 is a cross section of an ulcer or wound with sterile gel placed within a wound that has a sterile flexible adhesive film being applied to its outer surface and surrounding skin.

In FIG. 2, note that ulcer 14 is no longer an empty void of tissue, but has been filled with gel 30, which was dispensed from sterile packet of gel 26 (FIG. 1). Gel 30 fills the entire volume of ulcer 14 equal to the level of the surrounding superficial layers of skin 12. Filling of ulcer 14 with gel 30 provides a vehicle for transmission of ultrasound waves into ulcer 14 and subsequent reflected echoes from ulcer 14. Directing attention to skin 12, note that packet of adhesive flexible film 28, has been removed from envelope 20, (FIG. 1) opened and sterile flexible adhesive film 32 is being applied with its adhesive side down, a distance from ulcer 14 on one side. Then from this same site that is attached to skin 10, remaining adhesive flexible film 32 is lowered and advanced slowly to the opposite end of adhesive flexible film 32. This is a proper procedure to apply adhesive flexible film 32 to skin 12 and over ulcer 14 in a manner that eliminates trapping of air below adhesive flexible film 32.

Figure 3:
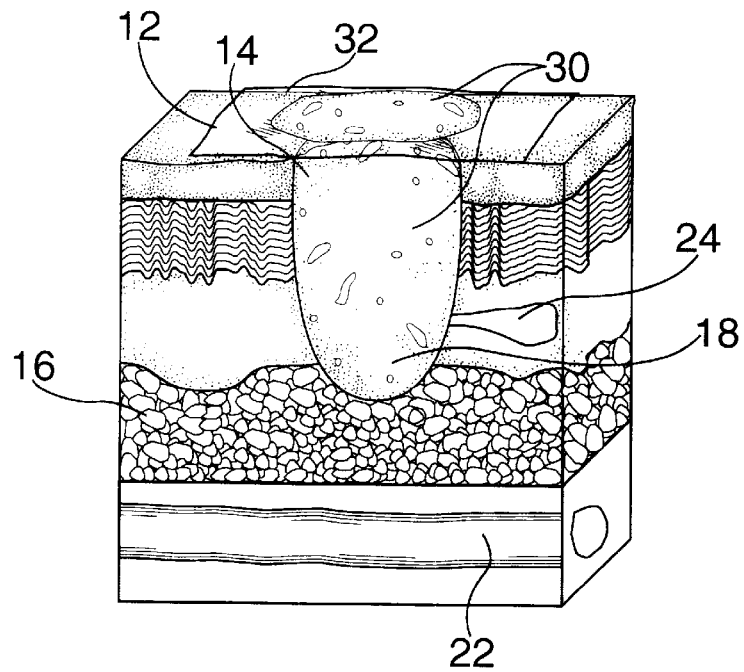
FIG. 3 is a cross section of an ulcer or wound revealing an sterile adhesive flexible film which is covering a wound and extending a distance around the wound with sterile contact gel above and below flexible film.

Directing ones attention to FIG. 3, observe that ulcer 14 has been filled with sterile gel 30 and adhesive flexible film 32 has is placed on top of skin 12 covering ulcer 14 with gel 30 inside. Note that adhesive flexible film 32 extends a distance from the edge of ulcer 14 on to normal skin 12. Having sealed ulcer 14, a layer of gel 30 is applied to superior surface of adhesive flexible film 32.

Figure 4:
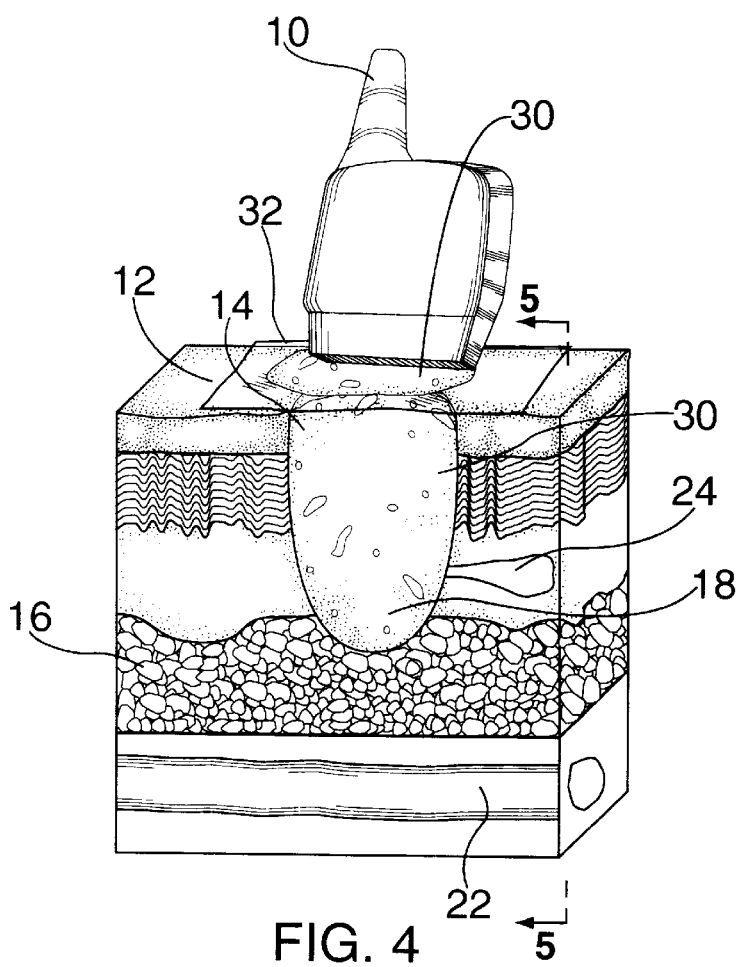
FIG. 4 is an example of a wound being scanned using a transducer in a position for scanning which is in contact with gel on the surface of adhesive flexible film.

FIG. 4 illustrates ulcer 14, now prepared with method and kit 32 for scanning with transducer 10. Note that transducer 10 is in contact with gel 30 on the outer non-adhesive surface of flexible film 32. Transducer 10 is shown in a proper position to evaluate skin 12, ulcer 14, subcutaneous tissues 16, subcutaneous abscess 24, surrounding tissue, and bone 22.

Figure 5:
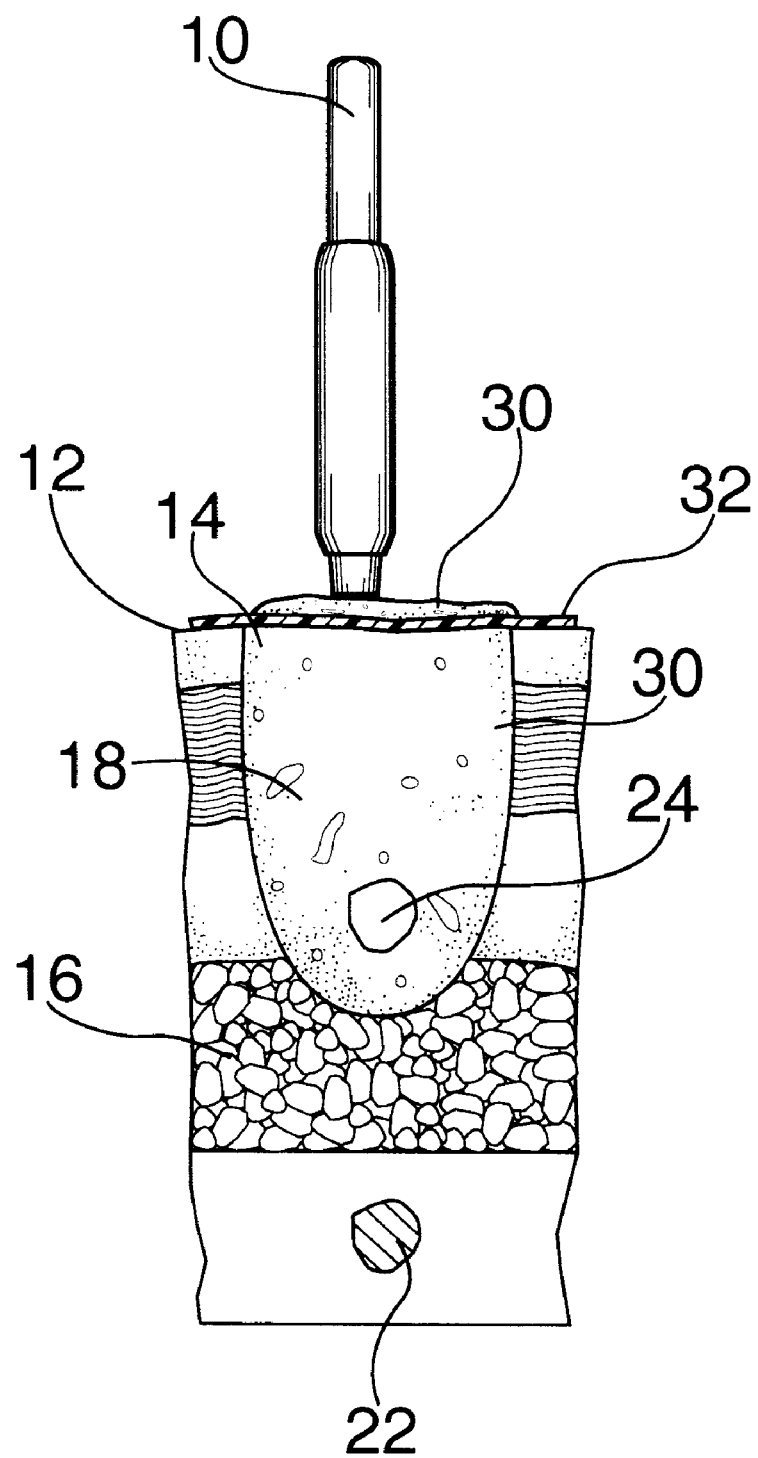
FIG. 5 is another view of the wound being scanned in FIG. 4 as taken in the direction of arrows 5—5 thereof.

FIG. 5 is a drawing of this method and kit 32 shown in FIG. 4 taken in the direction of arrows 5—5. FIG. 5 shows the relationship of transducer 10, which is in contact with gel 30 on the superior surface of flexible film 32. Below flexible film 32 gel 30 within ulcer 14 provides an acoustic window which is a vehicle that permits transmission of ultrasound from transducer 10 into ulcer 14, subcutaneous soft tissue 16, and bone 22. Subsequent returning echoes from ulcer 14, subcutaneous soft tissue 16, and bone 22 are received by transducer 10.

OPERATION—FIGS. 1, 2, 3, 4, 5

To illustrate how to evaluate wounds using this method and kit it is best demonstrated by using a more complex wound, ulceration 14. To begin, a health care practitioner must first prepare an area before an evaluation can proceed. Normally after applying gloves, a practitioner cleans ulceration 14 and skin 12 surrounding ulceration 14 followed by a rinse with sterile normal saline. Surrounding skin 12 surface is dried using sterile gauze or a sterile paper towel. Depending on the size of ulceration 14, kit 34 that is chosen should contain appropriate amounts of sterile gel 30 to fill ulceration 14 and a piece of sterile adhesive flexible film 32 which is large enough to cover the area to be examined as described.

Directing attention to kit 34 (FIG. 1) comprising of envelope 20 containing packet of sterile gel 26 and adhesive flexible film packet 28. When a practitioner opens envelope 20, one's first action is to open packet of gel 26. Gel 26 is preferably a sterile ultrasound transmission gel 30, water-soluble and a neutral ph factor. Such a gel 30, is considered safe to sensitive tissues found in ulcer 14, and is non-corrosive to transducer 10. It is felt that transmission gels containing chemicals such as those related to alcohol, peroxides, phenols, and other such germicidal properties are injurious to tissue and can damage transducer 10. Once open, gel packet 26 is gently squeezed over ulcer 14, filling ulcer 14 equal to the level of surrounding skin 12. (Many wounds are not like ulcer 14 in that they extend only into the superficial layers of skin 12. For such superficial, puncture, or closed wounds, a thin layer of gel 30 is applied over and around a wound site.) This method of applying gel 30 to ulcer's 14 surface first also protects delicate tissues found in ulcer 14 and other wounds from adhering to the adhesive surface of flexible film 32.

Continuing, an examiner then selects packet 28 with sterile adhesive flexible film 32, opens packet 28, and removes adhesive flexible film 32 (FIG. 2). Adhesive flexible film 32 has one surface with adhesive glue and its opposite surface is void of adhesive glue. Adhesive flexible film 32 is placed over ulcer 14 with adhesive side of flexible film 32 touching skin 12. Flexible film 32 should extend a distance past a wound's margin, and in this example, ulcer's 14 margin onto normal skin 12. When applying adhesive flexible film 32 to skin 12, it is best performed by first placing one end of adhesive flexible film 32 to dry intact skin 12, a distance from ulcer 14 containing sterile gel 30. From this same site that is attached to skin 12, remaining adhesive flexible film 32 is lowered and advanced slowly to the opposite end of adhesive flexible film 32. This method of applying adhesive flexible film 32 prevents air from being trapped below flexible film 32 surface and can be used for all types of wounds including ulcers, superficial, puncture, and closed wounds. A practitioner then applies a layer of gel 30 to the outer surface of flexible adhesive film 32 (FIG. 3). Ulcer 14 and surrounding tissues 16 are now ready to be examined. Flexible film 32, which is only microns thick, does not appear on an ultrasound scan. Method and kit 34 does not impede or reduce the scanning ability of transducer 10. Sterile adhesive flexible film 32 seals ulcer 14 with sterile gel 30 inside. Adhesive flexible film 32, insures that gel 30 is not pushed or moved away from a wound site or out of ulcer 14 during examination. This feature is important in that continuity is maintained between gel 30 and adhesive side of flexible film 32. Transducer 10 is placed over ulcer 14, making contact with gel 30 on outside non-adhesive surface of flexible film 32. Scanning of ulcer 14 commences (FIGS. 4–5). Ultrasound from transducer 10 traverses through gel 30 on outside non-adhesive surface of flexible film 32, continuing through flexible film 32, into gel 30 within ulcer 14, and finally to ulcer 14, subcutaneous tissue 16 and/or bone 22. Transducer 10 then listens for reflected echoes which return to transducer 10 following this same path in reverse. This method allows an examiner to view, evaluate, and measure, ulcer 14, subcutaneous tissue 16, and surface of bone 22. Transducer 10 is moved in any number of planes including longitudinal, transverse and oblique in order to survey ulcer 14, surrounding skin 12, and subcutaneous tissue 16. (It should be noted that wounds such as ulcer 14 usually contain microorganisms and therefore can contaminant ultrasound transducer 10. Likewise, transducer 10 also may contain microorganisms on its surface and can introduce germs into a wound. By using this technique, the risk of cross contamination is greatly reduced if not eliminated.)

Examining ulcer 14 and other superficial or closed wounds, using this method and kit 34, (FIGS. 1–4) a health care practitioner now has access to more information about that wound than any of the previous methods described above. A practitioner can painlessly measure a cavernous wound such as ulcer's 14 length, width and volume from the outer surface. An ultrasound unit computes this information and a permanent record can be made by videotape, optical disc, thermal video-paper, or other storage device. Clinical information beyond walls of ulcer 18 can be evaluated. None of the previous methods allow for a system to examine wound 14 beyond the surface without dyes, radiation or other invasive method. Besides measuring the thickness of the walls of ulcer 14, one can visualize cysts, sinus tract infections (channeling or tunneling of an infection), and subcutaneous abscess 24. Below the surface of closed or puncture wounds, such hidden pathologies are common but easily missed using previous methods. In addition, this novel method and kit 34 allows a practitioner to evaluate the surface of bone 22 to see if ulcer 14 has penetrated or disturbed the cortex of bone 22. Moreover, this method and kit 34, does not rely on blood flow to an area to carry dye or any other substance to permit scanning. Many wounds such as ischemic ulcerations have no blood flow. Having completed ulcer 14 and surrounding subcutaneous tissue 16 examination, the results are recorded on video paper, videocassette, or other digital storage device. An examining healthcare practitioner then removes sterile adhesive flexible film 32 and proceeds to rinse gel 30 from ulcer 14, or surface of a superficial or closed wound with sterile normal saline.

SUMMARY AND SCOPE

After reading the forestated description of a method and kit 32 to examine wounds, it becomes apparent that this invention will provide healthcare practitioners with a superior method to monitor wound care. This method has the ability to measure wound volume, surface area, height and width of ulcers, painlessly. This method and kit 32 enables an examiner to see beyond the base and walls of ulcer 14 along with that of superficial or closed wounds. This same method and kit 32 reveals maladies such as lateral channeling/tunneling of infections below skin 12 surface that cannot normally be seen using conventional methods of wound 14 evaluation. Furthermore, this method and kit 32 provides a avenue to monitor the surface of bone 22 tendons, ligaments, and other soft tissues around ulcer 14.

Also this novel method and kit 32:

Does not require a special transducer. It provides for a transducer normally used for musculoskeletal ultrasound.

Allows scanning of all wounds including those with poor or no circulation.

Permits examination of open wounds even if contaminated with microorganisms.

Prevents cross contamination of wound to transducer and transducer to wound.

Seals, and therefore contains infected gel eliminating the spread microorganisms during examination.

It vastly improves on present methods of evaluating wounds.

It is superior in the ability to record, document, and archive examination results.

Permits non-invasive examination of wounds below skin 12 surface.

Moreover, causes no injury to subcutaneous tissue 16 or bone 22.

Has application in doctor's offices, clinics, nursing homes, skilled care facilities, hospital emergency room and hospital clinics Can be used in veterinary medicine.

Finally, method and kit 34 described herein eliminates the need of injecting dyes, the use of radiation, or other expensive testing modalities such as CAT scans, PET scans, or MRI.

The above description shall not be construed as limiting in ways which this invention may be practiced but shall be inclusive of many other variation by those skilled in the art who's changes or modification could be made without departing from the broad interest, intent, and true spirit of this invention.

Method and Kit for Wound Evaluation

Having describe our invention what is claimed is:

1. A method of examining a cavernous wound and surrounding tissues which comprises:
   A. providing a sterile examining kit, said kit comprising a flexible film and a contact media,
   B. said contact media is applied to said cavernous wound surface in such quantity to fill said cavernous wound cavity,
   C. said flexible film is of sufficient size to cover and extend a distance beyond said cavernous wound boarder and surrounding tissues and,
   D. said flexible film has an adhesive means on one surface that allows said cavernous wound and surrounding tissues along with said contact media contained within, to be sealed below the adhesive surface of said flexible film,
   E. additional said contact media is applied to the outer surface of said flexible film and,
   F. said flexible film therefore, is sandwiched between said contact media which serves as an acoustic window that allows unimpeded transmission of ultrasound waves into said cavernous wound and surrounding tissues and,
   G. unimpeded reception of subsequent echoes from said cavernous wound and surround tissues, whereby a health practitioner protects and prevents transfer of contaminates during an exam, to record, examine, measure, and evaluate said cavernous wound and surrounding tissues that can not be see by human eye.

2. A method of examining a non-cavernous wound and surrounding tissues which comprises:
   A. providing a sterile examining kit, said kit comprising a flexible film and a contact media,
   B. said contact media is applied to said non-cavernous wound surface and surrounding tissues in such quantity to cover said non-cavernous wound and surrounding tissues with a thin layer of said contact media,
   C. said flexible film is of sufficient size to cover and extend a distance beyond said non-cavernous wound boarder and surrounding tissues and,
   D. said flexible film has an adhesive means on one surface that allows said non-cavernous wound and surrounding tissues along with said contact media contained within, to be sealed below the adhesive surface of said flexible film,
   E. additional said contact media is applied to the outer surface of said flexible film and,
   F. said flexible film therefore, is sandwiched between said contact media which serves as an acoustic window that allows unimpeded transmission of ultrasound waves into said non-cavernous wound and surrounding tissues and,
   G. unimpeded reception of subsequent echoes from said non-cavernous wound and surround tissues, whereby a health practitioner protects and prevents transfer of contaminates during an exam, to record, examine, measure, and evaluate said non-cavernous wound and surrounding tissues that can not be see by human eye.

3. A method of temporally protecting an area of human anatomy from the transfer of micro-organisms other contaminants during an ultrasound exam which comprises applying a flexible film of sufficient size to cover said area of human anatomy and said flexible film has an adhesive means applied to one surface that allows said flexible film to seal and protect said area of human anatomy, said flexible film allows for unimpeded transmission of ultrasound waves into said area of human anatomy and reception of subsequent echoes from said area human anatomy during examination.

* * * * *